US008440242B1

(12) United States Patent
Grady

(10) Patent No.: US 8,440,242 B1
(45) Date of Patent: May 14, 2013

(54) ALCOHOL METABOLIZING ASSISTING SUPPLEMENT

(76) Inventor: Paul Grady, Las Vegas, NV (US)

( * ) Notice: Subject to any disclaimer, the term of this patent is extended or adjusted under 35 U.S.C. 154(b) by 0 days.

(21) Appl. No.: 13/241,566

(22) Filed: Sep. 23, 2011

(51) Int. Cl.
*A01N 65/00* (2009.01)

(52) U.S. Cl.
USPC .......................................................... 424/725

(58) Field of Classification Search ........................ None
See application file for complete search history.

(56) References Cited

U.S. PATENT DOCUMENTS 8,153,561 B2 * 4/2012 Messerschmidt et al. .... 504/357

* cited by examiner

*Primary Examiner* — Michael Meller

(57) ABSTRACT

A alcohol metabolizing assisting supplement includes a mixture which includes humic and fulvic acids, L-Cysteine, L-Glutamine, thiamine mononitrate, and vitamins. The mixture is ingested after the consumption of alcohol to assist the body in quickly metabolizing the alcohol and to resist the negative effects of metabolizing alcohol.

2 Claims, No Drawings

ALCOHOL METABOLIZING ASSISTING SUPPLEMENT

BACKGROUND OF THE DISCLOSURE

1. Field of the Disclosure

The disclosure relates to alcohol metabolizing assisting mixtures and more particularly pertains to a new alcohol metabolizing assisting mixture for assisting the body in quickly metabolizing alcohol as well as replacing minerals and vitamins consumed by the body during the alcohol metabolizing process.

2. Summary of the Disclosure

An embodiment of the disclosure meets the needs presented above by generally comprising a mixture which includes humic and fulvic acids, L-Cysteine, L-Glutamine, thiamine mononitrate, and vitamins. To this mixture may further be included *Rhodiola rosea* extract and minerals including zinc. The mixture is ingested, typically after the consumption of alcohol, to assist the body in quickly metabolizing the alcohol and to resist the negative effects of metabolizing alcohol.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

DESCRIPTION OF THE PREFERRED EMBODIMENT

A new alcohol metabolizing assisting mixture embodying the principles and concepts of an embodiment of the disclosure will be described.

As best explained herein, the alcohol metabolizing assisting supplement 10 generally comprises a supplement which may be taken before, during or after consumption of alcohol (i.e. ethanol) to assist in the metabolizing of the alcohol by the body as well as to inhibit the side effects of metabolizing of alcohol. The supplement may be provided by any conventional delivery system. Such delivery systems may include a pill form, a liquid or a powder. While these deliver systems may simply be ingested as is, the liquid and powder, in particular, may be mixed with a fluid. For this reason, the powder and liquid may include additives such as flavorings or sweeteners which may not be required by the pill form.

The supplement is comprised of a mixture of a plurality of components. The mixture is then provided as a single dosage having an effective amount of each of the components to render to desired metabolic effects. The single dosage may include a plurality of the delivery systems. In particular, the single dosage may include multiple pills to provide for a comfortable means to swallow the supplement. For instance, in an example provided below, three pills may be provided such that their summed total of components is equal to the single dosage but that each pill includes approximately ⅓ of the single dosage. Additionally, it should be understood that the single dosage weights provided below are the weights of the active ingredients and therefore the total weight to be ingested may be increased by other additives not listed herein.

The mixture, in particular, may include in combination humic and fulvic acids (sometimes commonly referred to generically as organic acids), sodium ascorbate and/or zinc ascorbate to provide vitamine C, L-Cystein, L-Glutamine, thiamine monontitrate (vitamine B1), *Rhodiola Rosea* extract, silicon dioxide #63, calcium pantothenate (vitamine B5), niacinamide (vitamine B3), pyridoxine (vitamine B6), and zinc which may be supplied as zinc monomethionine, zinc ascorbate, or zinc citrate. Each of the components listed above are readily available and known, in particular, in the supplemental health market.

The supplement above and described more below have been shown to increase the body's ability to metabolize alcohol much more efficiently and while countering the side affects typically associated with the metabolizing of alcohol. With respect to the components, each plays a particular role to metabolize alcohol and/or assists in maintaining the body in a balanced state. Humic and fulvic acid are mixtures of organic acids and minerals, considered generally as anti-oxidants, which assist in neutralizing toxins in the body to assist the body in converting alcohol into acetic acid, water and carbon dioxide. Additionally, they are electrolytes which reverse dehydration more rapidly. The minerals found in humic and fulvic acids include trace minerals. The trace minerals in particular include magnesium, which is a mineral that is lost through alcohol metabolism. Other trace minerals of significance which are included are calcium and potassium. The trace minerals assist enzymatic reactions in the body, amino acid activation and DNA synthesis, boost energy production, and act as an alkalizing agent.

L-Cysteine and L-Glutamine are used by the liver to make glutathione. When alcohol is processed in the liver, acetaldehyde is formed which is further broken down to acetate by acetaldehyde dehydrogenase and glutathione. Low levels of glutathione leads to increased levels of acetaldehyde, which in turn causes customary negative effects of metabolizing alcohol including severe headaches and nausea.

Thiamine mononitrate, or vitamin B1 is required by the body to metabolize alcohol. When a person suffers from an aggravated deficiency of vitamin B1, the person will typically suffer from a headache, which may be directed to the forehead region. Vitamin B1 is also needed to convert food to energy in the body and provides proper nerve conduction without the over-excitement common after alcohol has depleted neurotransmitter balance in the body.

*Rhodiola rosea* is a plant known for its ability to increase the body's resistance to a variety of environmental and physical stressors. *Rhodiola rosea* has been found to provide enhanced oxygenation of the tissues. *Rhodiola rosea* has been shown to be effective in alleviating some of the adverse effects caused by alcohol consumption.

Vitamins C, B5 and B3 as well as zinc are used to supplement the body with required vitamins and minerals which are typically depleted when the body is stressed by acetaldehyde.

A single dosage of the mixture may include humic and fulvic acids, L-Cysteine, L-Glutamine, thiamine mononitrate, additional vitamins and/or minerals. The mixture may further include *Rhodiola rosea* extract. The vitamins may include calcium pantothenate, niancinamide and pyridoxine and the minerals may include zinc. The mixture may further include silicon dioxide.

The mixture may be provided such that the single dosage includes at least 50%, by weight, of humic and fulvic acids. More particularly, the humic and fulvic acids may comprise at least 50% by weight of the active ingredients of the mixture when the mixture includes active ingredients comprising humic and fulvic acids, L-Cysteine, L-Glutamine, thiamine mononitrate, vitamins, minerals and *Rhodiola rosea* extract.

In some embodiments of the mixture, the humic and fulvic acids will comprise at least 1050 mg of the single dosage and at least 150 mg of L-Cysteine.

An example of a single dosage includes:

| | |
|---|---|
| Humic and Fulvic acid | 1170 mg |
| Sodium Ascorbate and/or Zinc Ascorbate - total Vit C | 300 mg |
| L-Cysteine | 225 mg |
| L-Glutamine | 150 mg |
| Thiamine Mononitrate (B1) | 150 mg |
| *Rhodiola Rosea* Extract | 72 mg |
| Calcium Pantothenate (B5) | 60 mg |
| Niacinamide (B3) | 30 mg |
| Pyridoxine (Vit B6) | 30 mg |
| Zinc (Monomethionine, Ascorbate or Citrate) (Total Zinc) | 6 mg |
| Silicon Dioxide #63 | 54 mg |
| Total | 2250 mg |

The above may be provided in caplet or pill form wherein each pill includes only approximately ⅓ of the above amounts and a single dosage would include 3 pills. As mentioned, the above may be provided in a liquid form which may be consumed directly or mixed with another fluid. In such cases, flavorings and/or sweeteners may be added to the mixture. Alternatively, the mixture may be provided in a powder form that may also be mixed with a fluid. The powder may also include flavorings and/or sweeteners. The powder may be encapsulated within a conventional fluid dissolvable containment member as are well known in the art. Such a containment member would simply be dropped into a fluid and stirred such that the containment member dissolves and the powder mixes with the fluid.

Below is a study demonstrating the body's ability to quickly metabolize alcohol after consuming the mixture. The blood alcohol content "BAC" is shown for both natural declines as provided by Drunk Driving Defense (which can be viewed at www.drunkdrivingdefence.com). These figures have been found to substantially correlate to a wide number of similar studies and these figures are typically conventional in the art. The test was performed on 18 individuals who consumed the mixture after consumption of alcohol. The results below are an average of results.

| Time: | Starting BAC | +30 min BAC | +60 min BAC |
|---|---|---|---|
| Natural Metabolism: | 0.1458 | 0.1380 | 0.1308 |
| After Mixture Consumption | 0.1458 | 0.104 | 0.0610 |

30 minutes after consumption of the mixture, the average decrease in BAC was 29% with a low of 17.39% and a high of 47.13%. 60 minutes after consumption of the mixture, the average decrease in BAC was 58% with low of 43.17% and a high of 95.30%. These results are statistically significant as the natural reduction in BAC is 5% and 10%, respectively.

In some embodiments of the supplement 10, it may be advantageous to not have any additives which act as stimulants to the human body. Certain stimulants have been shown to have negative effects on the human body such as dehydration and an ability to fall asleep. In particular, the supplement 10 may be free of caffeine additives. It should be understood that this would include herbal sources of caffeine such as, but not limited to, Guarana (*Paullinia cupana*) and Yerba maté (*Ilex paraguariensis*). Finally, the mixture will be free of stimulants in general which may or may not include caffeine.

In use, the single dosage is consumed typically after a person has consumed alcohol. The mixture contained within the dosage will speed up the body's ability to metabolize alcohol and will thereafter provide the body with essential vitamins and minerals which were depleted during the body's metabolism of the alcohol. The person consuming the mixture will thereby recover much quickly from, or simply not experience, any negative effects of the alcohol.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A supplement for increasing the metabolism of alcohol in a patient in need thereof consisting essentially of therapeutically effective amounts of humic acid, fulvic acid, zinc ascorbate, L-cysteine, L-glutamine, thiamine mononitrate, *Rhodiola rosea* extract, calcium pantothenate, niacinamide, pyridoxine, zinc and silicon dioxide wherein said mixture is free of caffeine.

2. A supplement for increasing the metabolism of alcohol in a patient in need thereof consisting essentially of therapeutically effective amounts of humic acid, fulvic acid, sodium ascorbate, L-cysteine, L-glutamine, thiamine mononitrate, *Rhodiola rosea* extract, calcium pantothenate, niacinamide, pyridoxine, zinc and silicon dioxide wherein said mixture is free of caffeine.

* * * * *